(12) United States Patent
Tong et al.

(10) Patent No.: US 7,511,808 B2
(45) Date of Patent: Mar. 31, 2009

(54) ANALYTE STAGES INCLUDING TUNABLE RESONANT CAVITIES AND RAMAN SIGNAL-ENHANCING STRUCTURES

(75) Inventors: William M. Tong, Palo Alto, CA (US); Sean M. Spillane, Palo Alto, CA (US); Ellen R Tappon, Corvallis, OR (US); Phillip J. Kuekes, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/414,077

(22) Filed: Apr. 27, 2006

(65) Prior Publication Data
US 2007/0252983 A1    Nov. 1, 2007

(51) Int. Cl.
*G01J 3/44*    (2006.01)
(52) U.S. Cl. ...................................... 356/301
(58) Field of Classification Search ................. 356/301, 356/306, 307, 326
See application file for complete search history.

(56) References Cited

U.S. PATENT DOCUMENTS

| | | | |
|---|---|---|---|
| 4,121,167 A * | 10/1978 | Gibbs et al. ................. | 359/336 |
| 4,547,801 A | 10/1985 | Haisma et al. | |
| 4,674,878 A | 6/1987 | Vo-Dinh | |
| 4,935,939 A * | 6/1990 | Liau et al. ..................... | 372/98 |
| 4,944,985 A | 7/1990 | Alexander et al. | |
| 5,011,284 A | 4/1991 | Tedesco et al. | |
| 5,017,007 A | 5/1991 | Milne et al. | |
| 5,187,461 A | 2/1993 | Brommer et al. | |
| 5,216,686 A | 6/1993 | Holm et al. | |
| 5,242,828 A | 9/1993 | Bergstrom et al. | |
| 5,255,067 A | 10/1993 | Carrabba et al. | |
| 5,256,596 A | 10/1993 | Ackley et al. | |
| 5,293,392 A | 3/1994 | Shieh et al. | |
| 5,317,587 A | 5/1994 | Ackley et al. | |
| 5,335,240 A | 8/1994 | Ho et al. | |
| 5,359,618 A | 10/1994 | Lebby et al. | |
| 5,437,840 A | 8/1995 | King et al. | |
| 5,440,421 A | 8/1995 | Fan et al. | |
| 5,442,439 A | 8/1995 | Battey et al. | |

(Continued)

FOREIGN PATENT DOCUMENTS

| WO | WO 98/10289 A1 | 3/1998 |
|---|---|---|
| WO | WO 2004/059279 A2 | 7/2004 |

OTHER PUBLICATIONS

WebElements—Periodic Table Reference, http://webelements.com/periodicity/reflectivity/period_3sp.html.*

(Continued)

*Primary Examiner*—L. G Lauchman
*Assistant Examiner*—Rebecca C Slomski

(57) ABSTRACT

An analyte stage for use in a spectroscopy system includes a tunable resonant cavity that is capable of resonating electromagnetic radiation having wavelengths less than about 10,000 nanometers, a substrate at least partially disposed within the cavity, and a Raman signal-enhancing structure at least partially disposed within the tunable resonant cavity. A spectroscopy system includes such an analyte stage, a radiation source, and a radiation detector. Methods for performing Raman spectroscopy include using such analyte stages and systems to tune a resonant cavity to resonate Raman scattered radiation that is scattered by an analyte.

21 Claims, 9 Drawing Sheets

U.S. PATENT DOCUMENTS

| | | | |
|---|---|---|---|
| 5,468,656 | A | 11/1995 | Shieh et al. |
| 5,471,180 | A | 11/1995 | Brommer et al. |
| 5,527,712 | A | 6/1996 | Sheehy |
| 5,559,597 | A | 9/1996 | Battey et al. |
| 5,600,483 | A | 2/1997 | Fan et al. |
| 5,609,907 | A | 3/1997 | Natan |
| 5,677,924 | A | 10/1997 | Bestwick |
| 5,682,401 | A | 10/1997 | Joannopoulos et al. |
| 5,684,817 | A | 11/1997 | Houdre et al. |
| 5,706,306 | A | 1/1998 | Jiang et al. |
| 5,739,945 | A | 4/1998 | Tayebati |
| 5,771,253 | A | 6/1998 | Chang-Hasnain et al. |
| 5,772,905 | A | 6/1998 | Chou |
| 5,774,485 | A | 6/1998 | Stein |
| 5,784,400 | A | 7/1998 | Joannopoulos et al. |
| 5,837,552 | A | 11/1998 | Cotton et al. |
| 5,885,753 | A | 3/1999 | Crooks et al. |
| 5,943,128 | A | 8/1999 | Slater |
| 5,990,850 | A | 11/1999 | Brown et al. |
| 5,997,795 | A | 12/1999 | Danforth et al. |
| 5,998,298 | A | 12/1999 | Fleming et al. |
| 6,025,202 | A | 2/2000 | Natan |
| 6,058,127 | A | 5/2000 | Joannopoulos et al. |
| 6,067,156 | A | 5/2000 | Slater et al. |
| 6,134,043 | A | 10/2000 | Johnson et al. |
| 6,141,360 | A | 10/2000 | Kinugawa et al. |
| 6,149,868 | A | 11/2000 | Natan et al. |
| 6,154,591 | A | 11/2000 | Kershaw |
| 6,165,911 | A | 12/2000 | Calveley |
| 6,242,264 | B1 | 6/2001 | Natan et al. |
| 6,248,674 | B1 | 6/2001 | Kamins et al. |
| 6,274,293 | B1 | 8/2001 | Gupta et al. |
| 6,278,534 | B1 | 8/2001 | Arns |
| 6,291,924 | B1 | 9/2001 | Lau et al. |
| 6,339,030 | B1 | 1/2002 | Constant et al. |
| 6,351,306 | B1 | 2/2002 | Tedesco et al. |
| 6,365,059 | B1 | 4/2002 | Pechenik |
| 6,380,531 | B1 * | 4/2002 | Sugihwo et al. .......... 250/214.1 |
| 6,396,083 | B1 | 5/2002 | Ortiz et al. |
| 6,406,777 | B1 | 6/2002 | Boss et al. |
| 6,432,740 | B1 | 8/2002 | Chen |
| 6,434,180 | B1 | 8/2002 | Cunningham |
| 6,459,716 | B1 * | 10/2002 | Lo et al. .................... 372/50.1 |
| 6,525,880 | B2 | 2/2003 | Flanders et al. |
| 6,546,029 | B2 | 4/2003 | Sirbu et al. |
| 6,577,660 | B1 * | 6/2003 | Muroya ................... 372/50.11 |
| 6,579,721 | B1 | 6/2003 | Natan et al. |
| 6,608,685 | B2 | 8/2003 | Wood et al. |
| 6,608,716 | B1 | 8/2003 | Armstrong et al. |
| 6,623,977 | B1 | 9/2003 | Farquharson et al. |
| 6,649,683 | B2 | 11/2003 | Bell |
| 6,650,675 | B2 | 11/2003 | Sahara et al. |
| 6,678,289 | B2 | 1/2004 | Kim |
| 6,700,910 | B1 | 3/2004 | Aoki et al. |
| 6,711,200 | B1 | 3/2004 | Scherer et al. |
| 6,773,616 | B1 | 8/2004 | Chen et al. |
| 6,808,954 | B2 | 10/2004 | Ma et al. |
| 6,861,263 | B2 | 3/2005 | Natan |
| 6,867,900 | B2 | 3/2005 | Weisbuch et al. |
| 6,970,239 | B2 | 11/2005 | Chan et al. |
| 6,975,891 | B2 | 12/2005 | Pawluczyk |
| 6,989,897 | B2 | 1/2006 | Chan et al. |
| 2002/0182716 | A1 * | 12/2002 | Weisbuch et al. ........ 435/287.2 |
| 2003/0157732 | A1 | 8/2003 | Baker et al. |
| 2004/0077844 | A1 | 4/2004 | Jacobson et al. |
| 2005/0266583 | A1 * | 12/2005 | Farquharson et al. ....... 436/171 |
| 2006/0024502 | A1 * | 2/2006 | McFarland et al. .......... 428/408 |
| 2006/0055920 | A1 * | 3/2006 | Wang et al. ................. 356/301 |

OTHER PUBLICATIONS

Zhixun, Luo, Fang Yan, "SERS of gold/C60 (/C70) nano-clusters deposited on iron surface", Vibrational Spectroscopy 39 (2005) 151-156.*

Llao, PF, MB Stern, "Surface enhanced Raman scattering on gold and aluminum particle arrays", Optics Letters Oct. 1982 vol. 7 No. 10 483-485.*

U.S. Appl. No. 11/252,134, filed Oct. 17, 2005, entitled "Dynamically Variable Separation Among Nanoparticles for Nano-Enhanced Raman Spectroscopy (NERS) Molecular Sensing."

Blanco, Alvaro, et al., "Large-scale synthesis of a silicon photonic crystal with a complete three-dimensional bandgap near 1.5 micrometres," Nature, vol. 405, pp. 437-440, May 25, 2000.

Campbell, M., et al., "Fabrication of photonic crystals for the visible spectrum by holographic lithography," Nature, vol. 404, pp. 53-56, Mar. 2, 2000.

Chang-Hasnain, Connie J., "Tunable VCSEL," IEEE Journal on Selected Topics in Quantum Electronics, vol. 6, No. 6, pp. 978-987, Nov./Dec. 2000.

Collier, C.P., et al., "Reversible Tuning of Silver Quantum Dot Monolayers Through the Meltal-Insulator Transition," Science, vol. 277, pp. 1978-1981, Sep. 26, 1997.

Emory, Steven R., et al., "Screening and Enrichment of Metal Nanoparticles with Novel Optical Properties," J. Phys. Chem. B, vol. 102, No. 3, pp. 493-497, 1998.

Garcia-Vidal, F.J., et al., "Collective Theory for Surface Enhanced Raman Scattering," Physical Review Letters, vol. 77, No. 6, pp. 1163-1166, Aug. 5, 1996.

Gromov, Andrei, et al., "Fourier Transform Infrared and Raman Spectroscopic Study of Chromatographically Isolated Li@C60 and Li@C70," J. Phys. Chem. B, vol. 107, No. 41, pp. 11290-11301, 2003.

Joannopoulos, J.D., et al., "Photonic crystals: putting a new twist on light," Nature, vol. 386, pp. 143-149, Mar. 13, 1997.

Johnson, Steven G., et al., "Introduction to Photonic Crystals: Block's Theorem, Band Diagrams, and Gaps (But No Defects)," pp. 1-16, Feb. 3, 2003.

Kneipp, Katrin, et al., "Single Molecule Detection Using Surface-Enhanced Raman Scattering (SERS)," Physical Review Letters, vol. 78, No. 9, pp. 1667-1670, Mar. 3, 1997.

Lalanne, Ph., et al., "Two physical mechanisms for boosting the quality factor to cavity volume ratio of photonic crystal microcavities," Optics Express, Vo. 12, No. 3, pp. 458-467, Feb. 9, 2004.

Lu, Yu, et al., "High-Density Silver Nanoparticle Film with Temperature-Controllable Interparticle Spacing for a Tunable Surface Enhanced Raman Scattering Substrate," Nano Lett., vol. 5, No. 1, pp. 5-9, 2005.

Michaels, Amy M., et al., "Surface Enhanced Raman Spectroscopy of Individual Rhodamine 6G Molecules on Large Ag Nanocrystals," J. Am. Chem. Soc., vol. 121, No. 43, pp. 9932-9939, 1999.

Nie, Shuming, et al., "Probing Single Molecules and Single Nanoparticles by Surface-Enhanced Raman Scattering," Science, vol. 275, pp. 1102-1106, Feb. 21, 1997.

Qi, Minghao, et al., "A three-dimensional optical photonic crystal with designed point defects," Nature, vol. 429, pp. 538-542, Jun. 3, 2004.

Tao, Andrea, et al., "Langmuir-Blodgett Silver Nanowire Monolayers for Molecular Sensing Using Surface-Enhanced Raman Spectroscopy," Nano Letters, vol. 3, No. 9, pp. 1229-1233, 2003.

Vlasov, Yuril A., et al., "On-chip natural assembly of silicon photonic bandgap crystals," Nature, vol. 414, pp. 289-293, Nov. 15, 2001.

* cited by examiner

ANALYTE STAGES INCLUDING TUNABLE RESONANT CAVITIES AND RAMAN SIGNAL-ENHANCING STRUCTURES

FIELD OF THE INVENTION

The present invention relates to Raman spectroscopy. More particularly, the invention relates to Raman spectroscopy systems, analyte stages for use in Raman spectroscopy systems, and methods for performing Raman spectroscopy on an analyte.

BACKGROUND OF THE INVENTION

Raman spectroscopy is a technique for analyzing molecules or materials. In conventional Raman Spectroscopy, an analyte (or sample) that is to be analyzed is irradiated with high intensity monochromatic electromagnetic radiation provided by a radiation source, such as a laser. An electromagnetic radiation detector detects radiation that is scattered by the analyte. The characteristics of the scattered radiation provide information relating to the analyte.

Conventional Raman spectroscopy systems typically include an electromagnetic radiation source that is configured to emit incident electromagnetic radiation, an analyte stage on which an analyte may be positioned, and an electromagnetic radiation detector. The radiation detector is configured to detect at least a portion of scattered radiation that is scattered by the analyte. Raman spectroscopy systems also typically include various optical components positioned between the radiation source and the analyte stage, and between the analyte stage and the radiation detector. Such optical components may include lenses, filters, and apertures.

The radiation source may be a commercially available laser. The wavelength or wavelengths of incident electromagnetic radiation that may be emitted by the electromagnetic radiation source typically are within or near the visible region of the electromagnetic radiation spectrum.

The radiation detector receives and detects at least a portion of the scattered radiation that is scattered by an analyte disposed on the analyte stage. The detector may include a device for determining the wavelength of the scattered radiation (for example, a monochromator) and a device for determining the intensity of the scattered radiation (for example, a photomultiplier). Typically, the scattered radiation is scattered in all directions relative to the analyte stage.

Optical components positioned between the radiation source and the analyte stage are used to collimate, filter, or focus the incident radiation before the incident radiation impinges on the analyte stage. Optical components positioned between the analyte stage and the radiation detector are used to collimate, filter, or focus the scattered radiation.

An analyte may be provided on an analyte stage of a Raman spectroscopy system and irradiated with incident radiation emitted by a radiation source to perform Raman spectroscopy using a Raman spectroscopy system. As the incident radiation impinges on the analyte, at least some of the incident radiation will be scattered by the analyte. A majority of the photons of the incident radiation that impinge on the analyte are elastically scattered by the analyte. In other words, the scattered photons have the same energy, and thus the same wavelength, as the incident photons. This elastic scattering of photons is termed "Rayleigh scattering," and radiation consisting of these elastically scattered photons is termed "Rayleigh scattered radiation" or "Rayleigh radiation."

The Rayleigh scattering process can be further described with reference to the simplified Jablonski diagram shown schematically in FIG. 1, which illustrates various energy levels of a hypothetical analyte. In FIG. 1, energy levels of the analyte are represented as horizontal lines. As seen therein, the ground state energy level (the lowest energy level) is shown at the bottom of the diagram, excited vibrational energy states are shown just above the ground state, excited electronic energy states are shown at the top of the diagram, and virtual excited states are shown between the excited electronic states and the excited vibrational states. As seen in FIG. 1, Rayleigh scattering typically involves absorption of a single photon of the incident radiation by the analyte, which causes the analyte to transition from the ground state to a virtual state followed by relaxation to the ground state. As the analyte relaxes to the ground state, the analyte emits a photon of scattered radiation that has energy equal to that of the photon of the incident radiation. In this manner, the photon of the incident radiation is considered to have been elastically scattered.

In addition to the Rayleigh scattering of photons, a very small fraction of the photons of the incident radiation may be inelastically scattered by the analyte. Raman scattered radiation is also emitted from the analyte. Typically, only about 1 in $10^7$ of the photons of the incident radiation is inelastically scattered by the analyte. These inelastically scattered photons have a different wavelength than the photons of the incident radiation. This inelastic scattering of photons is termed "Raman scattering," and radiation consisting of Raman scattered photons is termed "Raman scattered radiation" or "Raman radiation." The photons of the Raman scattered radiation can have wavelengths less than, or more typically, greater than the wavelength of the photons of the incident radiation.

The Raman scattering process can be further described with reference to the simplified Jablonski diagram shown in FIG. 1. When a photon of the incident radiation collides with the analyte, energy can be transferred from the photon to the analyte, or from the analyte to the photon. When energy is transferred form the photon of the incident radiation to the analyte, the Raman scattered photon will have a lower energy and a corresponding longer wavelength than the incident photon. These Raman scattered photons having lower energy than the incident photons are collectively referred to in Raman spectroscopy as the "Stokes radiation." As seen in FIG. 1, 1st order Stokes Raman scattering typically involves absorption of a single photon of the incident radiation by the analyte, which causes the analyte to transition from a first energy state (for example, the ground state) to an excited virtual state. The analyte then relaxes to an excited vibrational state of higher energy than the first energy state. As the analyte relaxes to the excited vibrational state, the analyte emits a photon of scattered radiation that has less energy (and a longer wavelength) than the photon of the incident radiation. In this manner, the photon of the incident radiation is considered to have been inelastically scattered.

When energy is transferred from the analyte to a Raman scattered photon, the Raman scattered photon will have a higher energy and a corresponding shorter wavelength than the photon of the incident radiation. These Raman scattered photons, which have higher energy than the incident photons, are collectively referred to in Raman spectroscopy as the "anti-Stokes radiation." As seen in FIG. 1, 1st order anti-Stokes Raman scattering typically involves absorption of a single photon of the incident radiation by the analyte, which causes the analyte to transition from an excited vibrational energy state to an excited virtual state. The analyte then relaxes to a lower energy state (for example, the ground state) than the excited vibrational energy state. As the analyte relaxes to the lower energy state, the analyte emits a photon of scattered radiation that has more energy (and a shorter wavelength) than the photon of the incident radiation. In this manner, the photon of the incident radiation is considered to have been inelastically scattered.

The shift in energy (wavelength, frequency, or wave number) of the Raman scattered photons in relation to the Rayleigh scattered photons is known as the "Raman shift."

Raman scattering primarily involves a one photon excitation—one photon relaxation process. These Raman scattering processes are often referred to as "1st order" Raman scattering processes. However, multiple photon excitation—single photon relaxation processes are also observed and are referred to as "hyper Raman scattering" processes. Two photon excitation—one photon relaxation scattering processes are referred to as "2nd order" hyper Raman scattering processes, three-photon excitation—one photon relaxation processes are referred to as "3rd order" Raman scattering processes, etc. These higher order Raman scattering processes are often referred to as "harmonics."

In 2nd order scattering processes, a molecule of the analyte in an initial energy state absorbs the energy from two photons of the incident radiation causing an energy transition in the analyte to a virtual excited state, followed by relaxation to a final energy state and emission of a single scattered photon. If the final energy state is the same as the initial energy state, the scattering process is referred to as hyper Raleigh scattering. If the final energy state is higher than the initial energy state, the scattering process is referred to as 2nd order Stokes hyper Raman scattering. Finally, if the final energy state is lower than the initial energy state, the scattering process is referred to as 2nd order anti-Stokes hyper Raman scattering. The Stokes and anti-Stokes 2nd order hyper Raman scattering processes are also represented in the Jablonski diagram shown in FIG. 1.

Information may be obtained from hyper Raman scattered radiation that cannot be obtained from 1st order Raman scattered radiation. In particular, vibrational information may be suppressed in Raman scattered radiation due to symmetry issues, thereby resulting in what are often referred to as "silent modes." These silent modes may not be suppressed in the hyper Raman scattered radiation.

When an analyte is irradiated with incident radiation, the scattered radiation may include Raman scattered radiation, which may comprise 1st order Raman scattered radiation (Stokes and anti-Stokes) and higher order hyper Raman scattered radiation (Stokes and anti-Stokes), in addition to Rayleigh scattered radiation. The, Raman scattered radiation that is scattered by the analyte (including the hyper Raman scattered radiation) is often referred to as the "Raman signal."

The Raman signal is detected using the radiation detector. The wavelengths and corresponding intensity of the Raman scattered radiation may be determined and used to provide a Raman spectral graph. Analytes generate unique Raman spectral graphs. The unique Raman spectral graph obtained by performing Raman spectroscopy can be used to obtain information relating to the analyte including, but not limited to, the identification of an unknown analyte, or the determination of physical and chemical characteristics of a known analyte.

The number of Raman scattered photons that are scattered by an analyte is extremely small relative to the number of Rayleigh scattered photons, and the number of hyper Raman scattered photons is even smaller than the number of 1st order Raman scattered photons. Typical radiation detectors are capable of detecting the high-intensity Rayleigh scattered radiation in addition to the low-intensity Raman scattered radiation. The detection of the Raman scattered radiation may be difficult due to the high intensity of the Rayleigh scattered radiation. To overcome this difficulty, a radiation filter may be positioned between the analyte stage and the detector to prevent the Rayleigh scattered radiation from being detected by the detector, thus allowing only the Raman scattered radiation to be received by the detector. Commercially available notch filters may be used for such purposes.

After removal of the Rayleigh scattered radiation, the various wavelengths of Raman scattered radiation typically are spatially separated using a diffraction grating. The separated wavelengths of Raman scattered radiation typically are detected or imaged simultaneously using a charge coupled device (CCD) array. Alternatively, the wavelengths of Raman scattered radiation may be detected using a photomultiplier tube (PMT).

Surface-enhanced Raman spectroscopy (SERS) is a technique that allows for enhancement of the intensity of the Raman scattered radiation relative to conventional Raman spectroscopy (i.e., the number of Raman scattered photons that are scattered by an analyte). In SERS, the analyte typically is adsorbed onto or placed adjacent to what is often referred to as a SERS-active structure. SERS-active structures typically include a metal surface or structure. Interactions between the analyte and the metal surface may cause an increase in the intensity of the Raman scattered radiation.

Several types of metallic structures have been employed in SERS techniques to enhance the intensity of Raman scattered radiation that is scattered by an analyte. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface of gold or silver can enhance the Raman scattering intensity by factors of between $10^3$ and $10^6$.

Raman spectroscopy recently has been performed employing metal nanoparticles, such as nanometer scale needles, particles, and wires, as opposed to a simple roughened metallic surface. This process will be referred to herein as nano-enhanced Raman spectroscopy (NERS). Structures comprising nanoparticles that are used to enhance the intensity of Raman scattered radiation may be referred to as NERS-active structures. The intensity of the Raman scattered radiation that is scattered by an analyte adsorbed on such a NERS-active structure can be increased by factors as high as $10^{16}$.

BRIEF SUMMARY OF THE INVENTION

In one aspect, the present invention includes an analyte stage for use in a spectroscopy system. The analyte stage includes a tunable resonant cavity that is capable of resonating electromagnetic radiation having a wavelength of less than about 10,000 nanometers. A substrate and a Raman signal-enhancing structure are at least partially disposed within the tunable resonant cavity. The substrate is transparent to electromagnetic radiation having wavelengths between about 100 nanometers and about 10,000 nanometers.

In another aspect, the present invention includes a system for performing spectroscopy on an analyte. The system includes a source that is configured to provide incident radiation, an analyte stage, and a detector that is configured to detect Raman scattered radiation that is scattered by an analyte. The analyte stage includes a tunable resonant cavity that is capable of resonating electromagnetic radiation having a wavelength of less than about 10,000 nanometers. A substrate and a Raman signal-enhancing structure are at least partially disposed within the tunable resonant cavity. The substrate is transparent to electromagnetic radiation having wavelengths between about 100 nanometers and about 10,000 nanometers.

In yet another aspect, the present invention includes a method of performing Raman spectroscopy on an analyte. The method includes providing a tunable resonant cavity that is capable of resonating electromagnetic radiation having a wavelength less than about 10,000 nanometers, and providing a Raman signal-enhancing structure at least partially within the tunable resonant cavity. An analyte is provided within the tunable resonant cavity proximate the Raman signal-enhancing structure. The analyte is irradiated with incident electromagnetic radiation, and Raman scattered radiation that is scattered by the analyte is detected. The resonant cavity is tuned to resonate at least one wavelength of Raman scattered radiation.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The term "nanoparticle" as used herein means a particle of any shape having cross-sectional dimensions of less than about 100 nanometers. Examples of nanoparticles include, but are not limited to, nanodots (including quantum dots), nanowires, nanolines, nanocolumns, and nanospheres. The term "nanostructure" as used herein means a structure that includes one or more elements, features, or particles having cross-sectional dimensions of less than about 100 nanometers. For example, a nanostructure may include two or more nanoparticles positioned proximate to one another. As another example, a nanostructure may include a film having ridges or depressions formed in a surface thereof that have cross-sectional dimensions of less than about 100 nanometers. The term "analyte" as used herein means any molecule, molecules, material, substance, or matter that is to be analyzed by Raman spectroscopy.

The term "Raman signal-enhancing material" as used herein means a material that, when formed into appropriate geometries or configurations, is capable of increasing the number of Raman scattered photons that are scattered by an analyte when the analyte is located proximate to that material, and the analyte and material are subjected to electromagnetic radiation. Raman-enhancing materials include, but are not limited to, silver, gold, and copper. Raman-enhancing materials are used to form Raman signal-enhancing structures. The term "Raman signal-enhancing structure" as used herein means a structure that is capable of increasing the number of Raman scattered photons that are scattered by an analyte when the analyte is located proximate to the structure, and the analyte and structure are subjected to electromagnetic radiation. Raman signal-enhancing structures include SERS-active structures and NERS-active structures. The term "resonant cavity" as used herein means any spatially confined region in which at least one wavelength of electromagnetic radiation may resonate.

The illustrations presented herein are not meant to be actual views of any particular device or system, but are merely idealized representations which are employed to describe the present invention. Additionally, elements common between figures may retain the same numerical designation.

Figure 1:
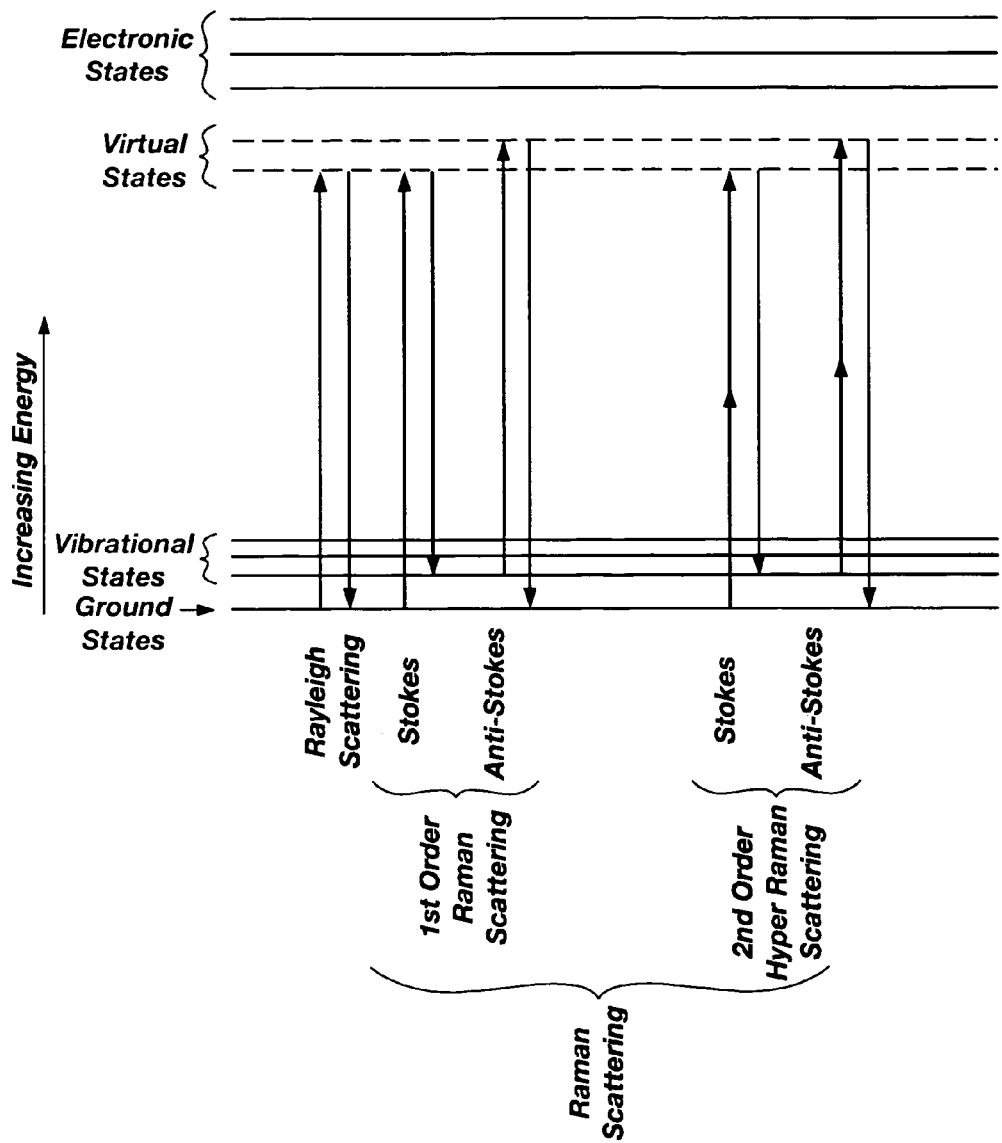
FIG. 1 is a Jablonski energy level diagram schematically representing Rayleigh and Raman scattering processes for a hypothetical analyte.
Figure 2:
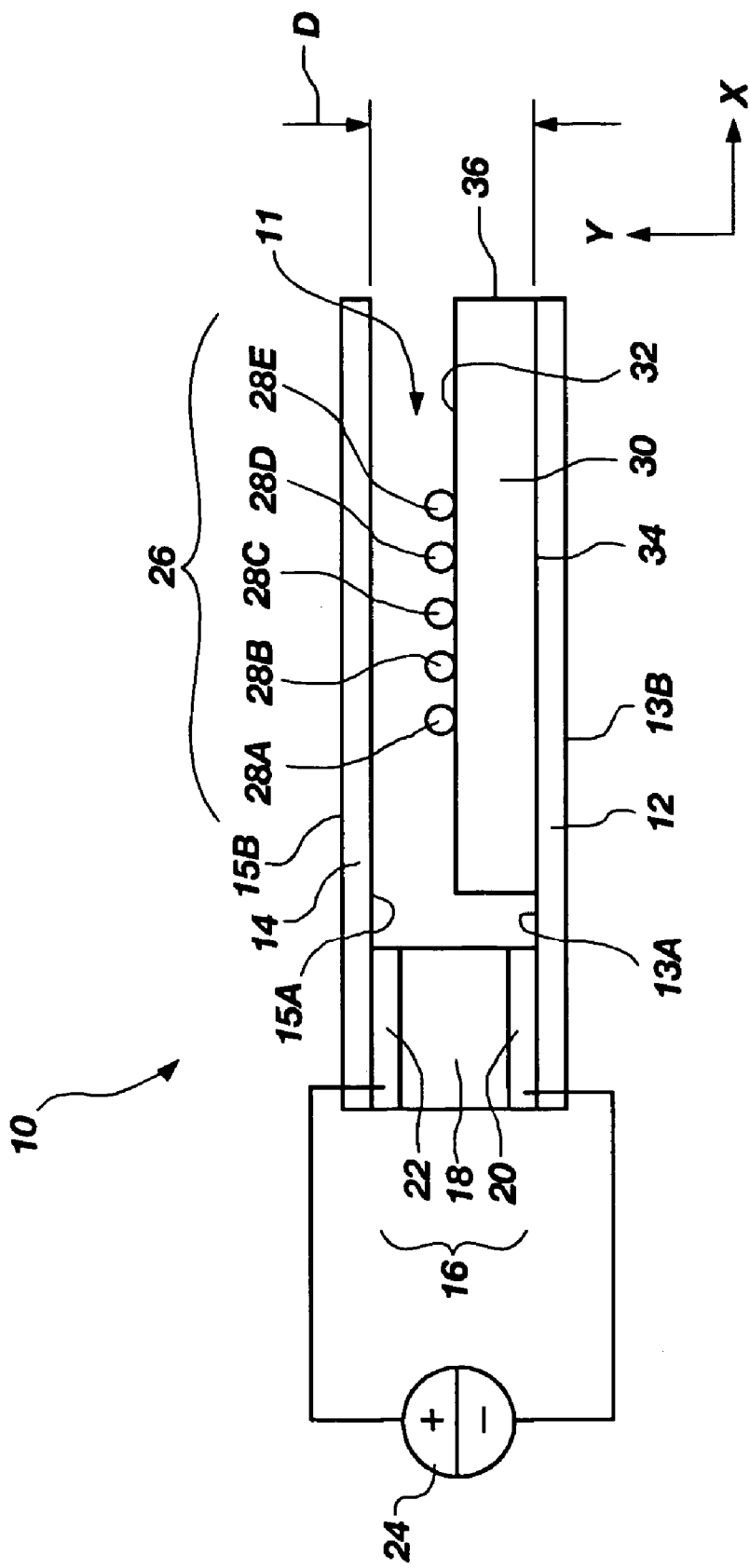
FIG. 2 is a side view of an embodiment of an analyte stage of the present invention.

An exemplary analyte stage 10 that embodies teachings of the present invention is shown in FIG. 2. The analyte stage 10 includes a tunable resonant cavity 11 and a Raman signal-enhancing structure 26 that is at least partially disposed within the tunable resonant cavity 11.

The tunable resonant cavity 11 may include a first mirror 12 and a second mirror 14. The first mirror 12 and the second mirror 14 each may be substantially planar, and the second mirror 14 may be oriented substantially parallel relative to the first mirror 12. The first mirror 12 may include a first major surface 13A and a second major surface 13B. Similarly, the second mirror 14 may include a first major surface 15A and a second major surface 15B. The first mirror 12 and the second mirror 14 each may include a material that is substantially transparent to wavelengths of electromagnetic radiation that are within an operating range of wavelengths of the tunable resonant cavity 11. For example, the first mirror 12 and the second mirror 14 each may include silica, diamond, or a transparent polymer material. A thin layer of reflective material may be provided on at least a portion of a surface of each of the first mirror 12 and the second mirror 14. For example, a thin layer of platinum or silver may be applied to each of the first major surface 13A of the first mirror 12 and the first major surface 15A of the second mirror 15A.

The reflectivity of the second mirror 14 may be less than one-hundred percent. In other words, at least some photons of electromagnetic radiation that have wavelengths that are within an operating range of wavelengths of the tunable resonant cavity 11 may be transmitted through the second mirror 14. To provide the second mirror 14 with a reflectivity of less than one-hundred percent, the thin layer of reflective material provided on the major surface 15A of the second mirror 14 may be sufficiently thin to allow some photons of electromagnetic radiation to pass through the second mirror 14. In contrast, the thin layer of reflective material provided on the major surface 13A of the first mirror 12 may be sufficiently thick to prevent substantially all photons of electromagnetic radiation having wavelengths that are within an operating range of wavelengths of the tunable resonant cavity 11 from passing through the first mirror 12. Alternatively, the first mirror 12 could have a reflectivity of less than one-hundred percent, or both the first mirror 12 and the second mirror 14 could have a reflectivity of less than one-hundred percent.

The reflective, first major surface 15A of the second mirror 14 may be separated from the reflective, first major surface 13A of the first mirror 12 by a distance D, as illustrated in FIG. 2.

The analyte stage 10 also may include a tuning device 16 that is configured to selectively vary the distance D separating the reflective, first major surface 15A of the second mirror 14 from the reflective, first major surface 13A of the first mirror 12. In one embodiment of the present invention, the tuning device 16 may include a piezoelectric transducer that is disposed between the first mirror 12 and the second mirror 14. One surface of the transducer may be attached to the first mirror 12 and another surface of the transducer may be attached to the second mirror 14.

By way of example and not limitation, the tuning device 16 may include a piezoelectric material 18, a first electrode 20, and a second electrode 22. The first electrode 20 and the second electrode 22 may be configured to apply a voltage across the piezoelectric material 18 between the first electrode 20 and the second electrode 22 to generate an electrical field. An electrical power source 24 may be provided and electrically connected to the first electrode 20 and the second electrode 22 to apply a voltage therebetween.

The piezoelectric material 18 of the tuning device 16 may comprise any known piezoelectric material such as, for example, lead zirconate titanate (PZT), barium titanate, or quartz. The first electrode 20 and the second electrode 22 may be formed from any conductive material including, but not limited to, silver, gold, copper and other metals or alloys.

The crystal structure of the piezoelectric material 18 may be oriented relative to the first electrode 20 and the second electrode 22 such that the piezoelectric material expands or contracts in a direction that causes the distance D separating the second mirror 14 from the first mirror 12 to vary in response to the electrical field generated between the first electrode 20 and the second electrode 22 using the power source 24 (i.e., the Y direction in FIG. 2). Applying a voltage having a first polarity across the piezoelectric material 18 between the first electrode 20 and the second electrode 22 may cause the piezoelectric material 18 to expand in the Y direction, and applying a voltage having an second, opposite polarity across the piezoelectric material 18 between the first electrode 20 and the second electrode 22 may cause the piezoelectric material 18 to contract in the Y direction.

As the first mirror 12 and the second mirror 14 each are attached to the tuning device 16, the tuning device 16 may be used to selectively vary the distance D separating the second mirror 14 from the first mirror 12 by selectively controlling the magnitude and polarity of the voltage applied between the first electrode 20 and the second electrode 22 using the power source 24. The distance D may be varied between a maximum distance D defining an upper limit of operation and a minimum distance D defining a lower limit of operation. The upper limit and the lower limit of the distance D may define the operating range of wavelengths of the tunable resonant cavity 11, as will be subsequently discussed in further detail. Furthermore, the second mirror 14 may remain oriented substantially parallel relative to the first mirror 12 while the distance D is varied.

The analyte stage 10 additionally may include a transparent substrate 30 that is at least partially disposed between the first mirror 12 and the second mirror 14. The transparent substrate 30 may include a material that is substantially transparent to wavelengths of electromagnetic radiation that are within an operating range of wavelengths of the tunable resonant cavity 11. The transparent substrate 30 may be substantially planar and may include a first major surface 32, a second major surface 34, and at least one lateral surface 36. The transparent substrate 30 may include a material that is substantially transparent to wavelengths of electromagnetic radiation that are within the operating range of wavelengths of the tunable resonant cavity 11. The transparent substrate 30 may include, for example, silica, silicon nitride, calcium fluoride, diamond, or a transparent polymer material.

The transparent substrate 30 additionally may comprise a material that will emit Raman scattered radiation at known wavelengths that are within the operating range of wavelengths of the tunable resonant cavity 11. These known wavelengths of Raman scattered radiation may be used to calibrate a Raman spectroscopy system or components of a Raman spectroscopy system (such as a radiation detector) that may be used in conjunction with the analyte stage 10 to perform Raman spectroscopy on an analyte. For example, the transparent substrate 30 may be selectively doped with a predetermined amount of $C_{60}$, which is known to emit Raman scattered radiation at a known wavelength of about 6,849 nanometers.

The transparent substrate 30 may have a thickness such that a Raman signal-enhancing structure 26 disposed on the first major surface 32 thereof is located proximate the center of the tunable resonant cavity 11. In other words, a distance from the Raman signal-enhancing structure 26 to the first mirror 12 may be substantially equal to a distance from the Raman signal-enhancing structure 26 to the second mirror 14.

The Raman signal-enhancing structure 26 that is at least partially disposed within the tunable resonant cavity 11 may include a NERS-active structure. By way of example and not limitation, the NERS-active structure may include a plurality of nanoparticles, such as the nanoparticles 28A, 28B, 28C, 28D, and 28E shown in FIG. 2. Each of the nanoparticles 28A-28E may include a Raman signal-enhancing material such as, for example, gold, platinum, or silver. The nanoparticles 28A-28E may have a substantially spherical shape, as shown in FIG. 2. Alternatively, the nanoparticles 28A-28E may have other shapes including, but not limited to semi-spherical shapes, pyramidal shapes, and cubicle shapes. Furthermore, the nanoparticles 28A-28E may be elongated having cross-sectional areas that have, for example, circular shapes, triangular shapes, or rectangular shapes.

The nanoparticles 28A-28E may be provided at either random or predetermined positions within the tunable resonant cavity 11. The nanoparticles 28A-28E may be selectively positioned within the tunable resonant cavity 11 to provide a distance between adjacent nanoparticles 28A-28E of between about 1 nanometer and about 15 nanometers.

In one particular embodiment of the present invention, the nanoparticles 28A-28E may be formed directly on the first major surface 32 of the transparent substrate 30 using known epitaxial or lithographic techniques. As one example, a thin layer of Raman signal enhancing material may be deposited on the first major surface 32 of the transparent substrate 30 using physical vapor deposition. A selected portion of the thin layer of Raman signal enhancing material then may be removed using a chemical etch, an ion beam, or an electron beam, the remaining portions of the thin layer of Raman signal enhancing material defining the nanoparticles 28A-28E of the Raman signal-enhancing structure 26.

Figure 3:
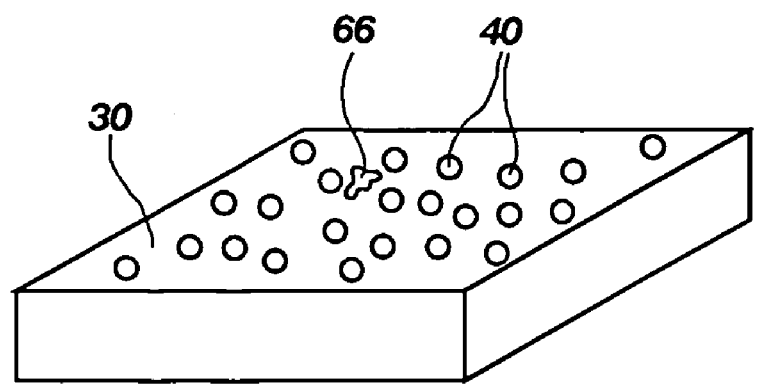
FIG. 3 is a perspective view of an exemplary Raman signal-enhancing structure that may be used in analyte stages that embody teachings of the present invention.
Figure 4:
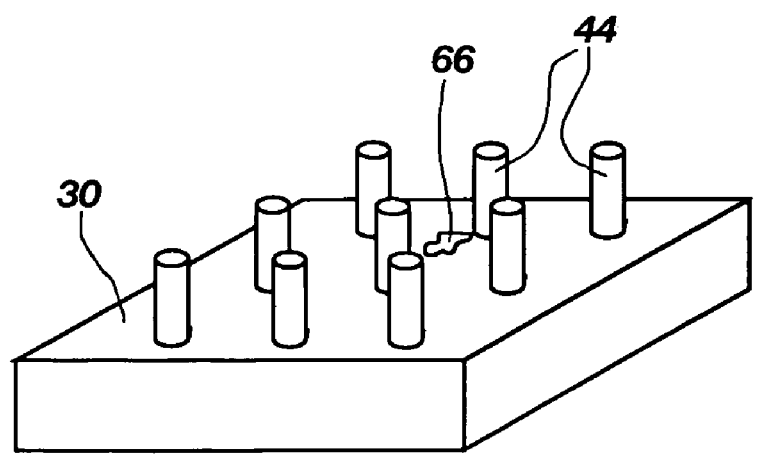
FIG. 4 is a perspective view of another embodiment of a Raman signal-enhancing structure that may be used in analyte stages.

FIGS. 3-4 illustrate additional embodiments of Raman signal-enhancing structures that may disposed within a tunable resonant cavity of an analyte stage according to the present invention. As seen in FIG. 3, nanoparticles 40 having a substantially spherical shape may be randomly dispersed over a major surface of a transparent substrate 30. The nanoparticles 40 may include a Raman signal-enhancing material to provide a NERS-active structure. As shown in FIG. 4, nanoparticles 44 having a substantially cylindrical shape may extend from a major surface of a transparent substrate 30 in a direction substantially perpendicular thereto. Furthermore, the nanoparticles 44 may be provided at selected, predetermined locations on the surface of the transparent substrate 30. The nanoparticles 44 also may include a Raman signal-enhancing material to provide a NERS-active structure. An analyte 66 is shown positioned at a location proximate the nanoparticles 40 in FIG. 3 and at a location proximate the nanoparticles 44 in FIG. 4. Other configurations of Raman signal-enhancing structures including any known SERS-active structures and NERS-active structures may be positioned within tunable resonant cavities as described herein to provide analyte stages that embody teachings of the present invention.

In addition to multiple nanoparticles, the Raman signal-enhancing structure of an analyte stage may include a unitary nanostructure that includes a Raman signal-enhancing material. Analyte stages, such as the analyte stage 10 shown in FIG. 2, may be used in spectroscopy systems to provide spectroscopy systems.

Figure 5:
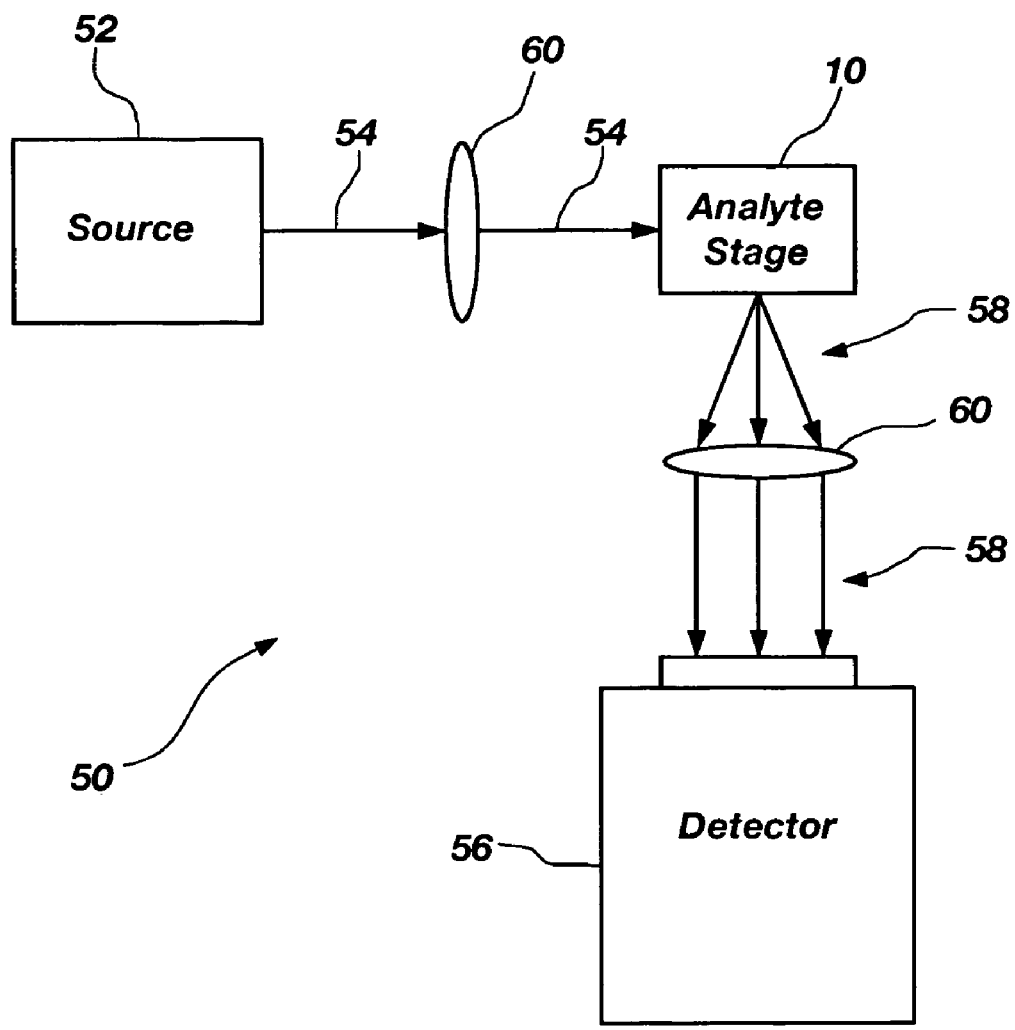
FIG. 5 is a schematic diagram of an embodiment of a spectroscopy system of the present invention.

An embodiment of a Raman spectroscopy system 50 is illustrated schematically in FIG. 5. The Raman spectroscopy system 50 may include an electromagnetic radiation source 52 configured to provide incident electromagnetic radiation 54, an electromagnetic radiation detector 56 that is configured to detect Raman scattered radiation 58 that is scattered by an analyte, and an analyte stage, such as, for example, the analyte stage 10 shown in FIG. 2. The Raman spectroscopy system 50 also may include various optical components 60 (such as, for example, apertures, lenses, and filters) positioned between the electromagnetic radiation source 52 and the analyte stage 10, and between the analyte stage 10 and the radiation detector 56.

The radiation source 52 may include any suitable source for emitting incident electromagnetic radiation 54 at a desired wavelength and may be capable of emitting a tunable wavelength of incident electromagnetic radiation 54. For example, commercially available semiconductor lasers, helium-neon lasers, carbon dioxide lasers, radiation emitting diodes, incandescent lamps, vertical cavity surface emitting lasers, edge emitting lasers, and many other known radiation emitting sources can be used as the electromagnetic radiation source 52. If necessary, a radiation filter may be used in conjunction with the electromagnetic radiation source 52 to provide monochromatic incident electromagnetic radiation 54. The wavelengths that are emitted by the electromagnetic radiation source 52 may be any suitable wavelength for performing Raman spectroscopy on the analyte, and may be within or near the visible region of the electromagnetic radiation spectrum.

The detector 56 receives and detects the Raman scattered radiation 58 that includes Raman scattered photons that are scattered by an analyte disposed within the tunable resonant cavity 11 of the analyte stage 10 proximate the Raman signal-enhancing structure 26 (see FIG. 2). The detector 56 may include a device for determining the wavelength of the Raman scattered radiation 58, such as, for example, a monochromator, and a device for determining the intensity of the Raman scattered radiation 58, such as, for example, a photomultiplier. Typically, the Raman scattered radiation 58 is scattered in all directions relative to the analyte stage 10.

Optical components 60 positioned between the electromagnetic radiation source 52 and the analyte stage 10 can be used to collimate, filter, or focus the incident electromagnetic radiation 54 before the incident electromagnetic radiation 54 impinges on the analyte stage 10. Optical components 60 positioned between the analyte stage 10 and the detector 56 can be used to collimate, filter, or focus the Raman scattered radiation 58. The optical components 60 may include, for example, apertures, lenses, and filters.

Figure 6:
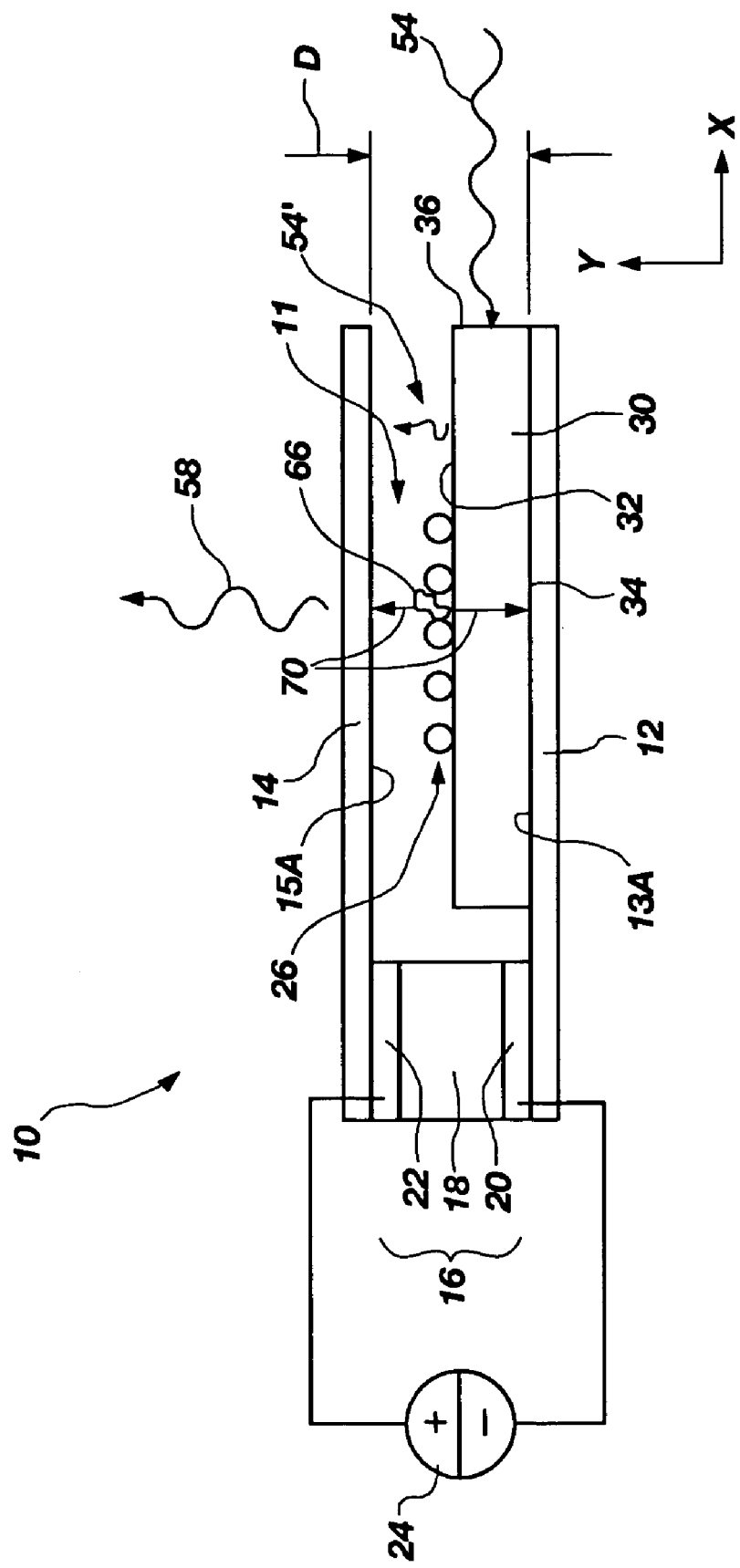
FIG. 6 is a side view of the analyte stage shown in FIG. 2, enhanced to illustrate principles of operation thereof.

FIG. 6 again illustrates the analyte stage 10 shown in FIG. 2 and illustrates principles of operation thereof. To perform Raman spectroscopy on an analyte using the Raman spectroscopy system 50, an analyte 66 may be provided within the tunable resonant cavity 11 proximate the Raman signal-enhancing structure 26, as shown in FIG. 6. The analyte 66 may be irradiated with incident electromagnetic radiation 54 provided by an electromagnetic radiation source. The incident electromagnetic radiation 54 may impinge directly on the analyte 66 without first passing through the first mirror 12 or the second mirror 14.

As shown in FIG. 6, a lateral side 36 of the transparent substrate 30 may be irradiated with incident electromagnetic radiation 54. The incident electromagnetic radiation 54 may propagate substantially through the transparent substrate 30, and may experience total internal reflection at the first major surface 32 and the second major surface 34 of the transparent substrate 30. Evanescent incident electromagnetic radiation 54', however, may be emitted from the first major surface 32 of the transparent substrate 30. This evanescent incident electromagnetic radiation 54' may impinge on the analyte 66.

The analyte 66 may scatter at least some of the photons of the evanescent incident electromagnetic radiation 54' within the tunable resonant cavity 11. At least some of these scattered photons may be inelastically scattered, thereby generating Raman scattered radiation 58 within the tunable resonant cavity 11.

The tunable resonant cavity 11 may behave as a Fabry-Perot resonator. Raman scattered radiation 58 that is scattered by the analyte in directions substantially perpendicular to the first major surface 13A of the first mirror 12 and the first major surface 15A of the second mirror 14 may reflect back and forth between the first mirror 12 and the second mirror 14 in the directions indicated by the directional arrows 70. If the distance D separating the second mirror 14 from the first mirror 12 is not equal to an integer multiple of one-half of the wavelength of the Raman scattered radiation 58, the rays of Raman scattered radiation 58 reflecting back and forth between the first mirror 12 and the second mirror 14 may interfere destructively. If, however, the distance D separating the second mirror 14 from the first mirror 12 is equal to an integer multiple of one-half of the wavelength of the Raman scattered radiation 58, the rays of Raman scattered radiation 58 reflecting back and forth between the first mirror 12 and the second mirror 14 may interfere constructively, thereby increasing the intensity or power of the Raman scattered radiation 58 within the tunable resonant cavity 11. As the reflectivity of the second mirror 14 is less than one-hundred percent, some of the resonating Raman scattered radiation 58 may pass through the second mirror 14 as shown in FIG. 6 and may be detected.

While the analyte 66 is being irradiated with incident electromagnetic radiation 54 or the evanescent incident electromagnetic radiation 54', the distance D separating the second mirror 14 from the first mirror 12 may be selectively varied by selectively controlling the magnitude and polarity of the voltage applied between the first electrode 20 and the second electrode 22 using the power source 24 until the tunable resonant cavity 11 is tuned to resonate the various wavelengths of Raman scattered radiation 58 that are scattered by the analyte. For example, the distance D may be may be selectively continuously varied between the maximum distance D defining the upper limit of operation of the tunable resonant cavity 11 and the minimum distance D defining the lower limit of operation of the tunable resonant cavity 11.

In one particular embodiment of the invention, the maximum distance D may be between about 10,000 nanometers and the minimum distance may be about 200 nanometers. In this particular embodiment, the resonant cavity is configured to resonate electromagnetic radiation wavelengths less than about 10,000 nanometers. In yet another particular embodiment of the invention, the maximum distance may be about 1,500 nanometers and the minimum distance may be about 300 nanometers. In this particular embodiment, the resonant cavity is configured to resonate electromagnetic radiation wavelengths less than about 1,500 nanometers.

The Raman scattered radiation 58 may be continuously detected while selectively continuously varying the distance D between the maximum distance and the minimum distance. In this manner, a unique Raman spectral graph of the analyte 66 may be obtained and used to identify or characterize the analyte 66.

The tunable resonant cavity 11 of the analyte stage 10 behaves as a wavelength dispersive element, since only particular wavelengths of electromagnetic radiation will resonate within the tunable resonant cavity 11 at for any particular distance D. By varying or scanning the distance D over a range of distances, each wavelength of Raman scattered radiation may be individually detected and the need for a separate wavelength dispersive element, such as a grating, is eliminated. In other words, by employing analyte stages that embody teachings of the present invention (such as the analyte stage 10 shown in FIGS. 2, and 6), spectroscopy systems may be provided that do not include a grating or other wavelength dispersive element apart from the analyte stage.

Resonant cavities are often characterized by a quality factor Q, which may be defined as the ratio of the total energy stored in the resonant cavity to the energy being dissipated in the resonant cavity. The analyte stage 10 may have a quality factor Q of greater than about 100 for particular wavelengths of electromagnetic radiation.

Figure 7:
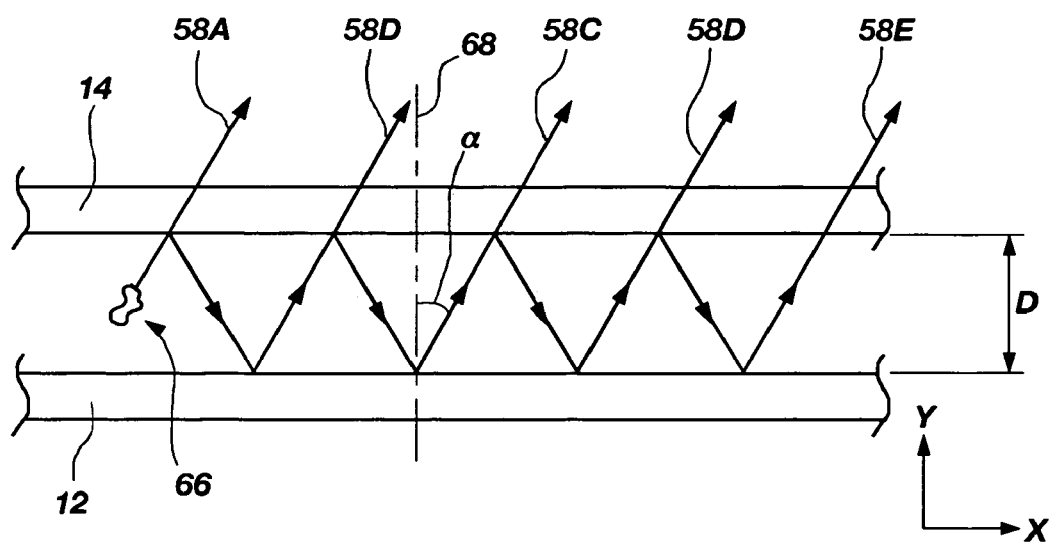
FIG. 7 is a simplified diagram of elements of the analyte stage shown in FIG. 2 illustrating additional principles of operation thereof.

The tunable resonant cavity 11 may also behave as a Fabry-Perot interferometer. FIG. 7 is a simplified diagram illustrating the first mirror 12, the second mirror 14, and the analyte 66 positioned at a location between the first mirror 12 and the second mirror 14. Rays of Raman scattered radiation 58A-58E that have been scattered by the analyte 66 at an angle a relative to a line 68 that is normal to the first mirror 12 and the second mirror 14 are also shown in FIG. 7. As the reflectivity of the second mirror is less than one-hundred percent, at least some Raman scattered radiation may be transmitted through the second mirror 14 after each successive reflection between the mirrors. If the Raman scattered radiation has a wavelength $\lambda$, then the rays of Raman scattered radiation 58A-58E may interfere in a purely constructive manner only when $2D\cos\alpha = m\lambda$, where m is the order of interference (an integer greater than or equal to 1). If $2D\cos\alpha$ does not equal $m\lambda$, then the rays of Raman scattered radiation 58A-58E may interfere destructively and may be dissipated as they pass through the second mirror 14.

Since Raman scattered radiation is scattered in all directions (all angles $\alpha$) relative to the analyte 66, there may be multiple angles at which the Raman scattered radiation may interfere constructively. Most of the angles, however, will not interfere in a purely constructive manner and may be dissipated.

In the case where a is equal to zero (the radiation is scattered directly perpendicular to the first mirror 12 and the second mirror 14), $\cos\alpha$ is equal to 1 and the condition for constructive interference becomes $2D = m\lambda$, or $D = \frac{1}{2}m\lambda$, which means that the distance D must equal one-half of an integer multiple of the wavelength of the Raman scattered radiation, as previously discussed in relation to FIG. 6.

In light of the above principles, Raman scattered radiation that is scattered in directions other than substantially perpendicular to the first mirror 12 and the second mirror 14 (i.e., the Y direction in FIG. 7) may be substantially limited. This may provide substantially collimated Raman scattered radiation 58 (FIG. 6) passing through the second mirror 14, which may eliminate the need for a separate collimator as part of a Raman system including the analyte stage 10 to conduct Raman spectroscopy.

As previously discussed, the radiation detector 56 (FIG. 5) may be calibrated using the transparent substrate 30 prior to performing Raman spectroscopy on the analyte 66. If the transparent substrate 30 includes a material known to emit Raman scattered radiation 58 at known wavelengths, a surface of the transparent substrate 30 may be irradiated with incident electromagnetic radiation 54 emitted by the electromagnetic radiation source 52. The Raman scattered radiation 58 may be scattered by the material at known wavelengths of electromagnetic radiation. The distance D may be selectively varied by selectively controlling the magnitude and polarity of the voltage applied between the first electrode 20 and the second electrode 22 until the tunable resonant cavity 11 is tuned to resonate the Raman scattered radiation 58. The known wavelengths of resonating Raman scattered radiation 58 may be detected and used to calibrate the radiation detector 56.

Figure 8:
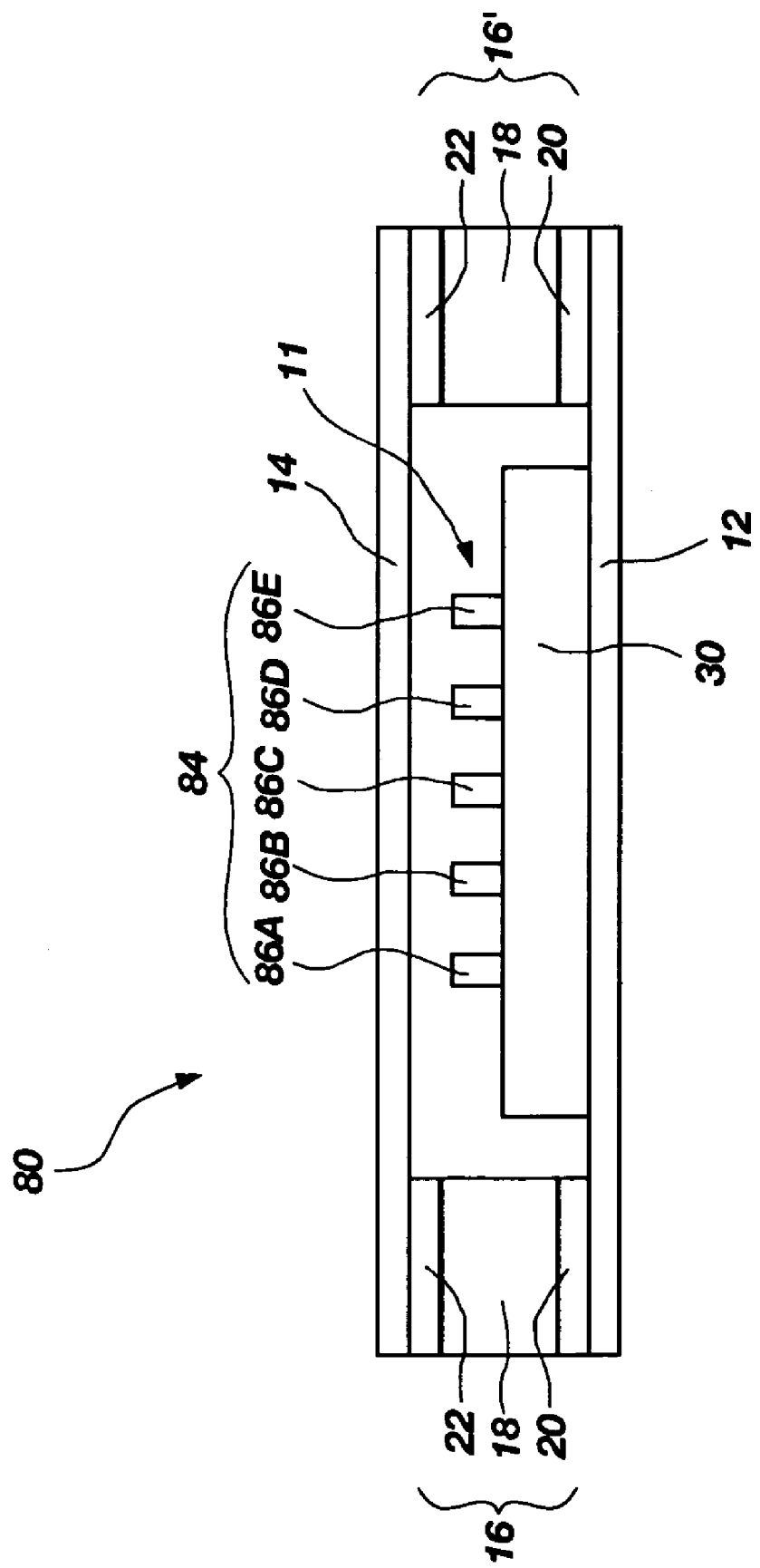
FIG. 8 is a side view of another embodiment of an analyte stage of the present invention.

Another embodiment of an analyte stage 80 of the present invention is shown in FIG. 8. The analyte stage 80 is substantially similar to the analyte stage 10 previously described herein in relation to FIGS. 2, and includes a tunable resonant cavity 11 and a Raman signal-enhancing structure 84 that is at least partially disposed within the tunable resonant cavity 11. The tunable resonant cavity 11 may include a first mirror 12 and a second mirror 14. Each of the first mirror 12 and the second mirror 14 may be substantially planar, and the second mirror 14 may be oriented substantially parallel relative to the first mirror 12.

The analyte stage 80 also may include a first tuning device 16 disposed on a first side of the tunable resonant cavity 11 and a second tuning device 16' disposed on a second side of the tunable resonant cavity 11. For example, the second tuning device 16' may be disposed on an opposite side of the tunable resonant cavity 11 relative to the first tuning device 16, as shown in FIG. 8, to provide additional support to the second mirror 14. The first tuning device 16 and the second tuning device 16' may be configured to selectively vary the distance separating the second mirror 14 from the first mirror 12. In one particular embodiment of the present invention, the first tuning device 16 and the second tuning device 16' each may include a piezoelectric transducer that is disposed between the first mirror 12 and the second mirror 14.

By way of example and not limitation, the first tuning device 16 and the second tuning device 16' each may include a piezoelectric material 18, a first electrode 20, and a second electrode 22. In each of the first tuning device 16 and the second tuning device 16', the first electrode 20 and the second electrode 22 may be configured to apply a voltage across the piezoelectric material 18 between the first electrode 20 and the second electrode 22 to generate an electrical field therebetween. An electrical connection may be provided between the first electrode 20 of the first tuning device 16 and the first electrode 20 of the second tuning device 16', and an electrical connection may be provided between the second electrode 22 of the first tuning device 16 and the second electrode 22 of the second tuning device 16'. An electrical power source 24 (shown in FIG. 2) may be provided and configured to apply a voltage between the first electrodes 20 and the second electrodes 22. In this configuration, a substantially similar electrical field may be generated across the piezoelectric material 18 of the first tuning device 16 and the piezoelectric material 18 of the first tuning device 16'. This may provide uniform displacement of the second mirror 14 relative to the first mirror 12, thereby allowing the second mirror 14 to maintain a substantially parallel relationship to the first mirror 12.

The Raman signal-enhancing structure 84 shown in FIG. 8 may include a plurality of nanoparticles 86A-86E that have a substantially cylindrical shape. The nanoparticles 86A-86E may extend from a surface of a transparent substrate 30 in a direction substantially perpendicular thereto. Furthermore, the nanoparticles 86A-86E may be provided at selected, predetermined locations on the surface of the transparent substrate 30. The nanoparticles 86A-86E also may include a Raman signal-enhancing material.

The analyte stage 80 shown in FIG. 8 may be used in a spectroscopy system such as, for example, the previously described spectroscopy system 50 shown in FIG. 5, in substantially the same manner as that previously described in relation to the analyte stage 10 and FIG. 6. The analyte stage 10 shown in FIG. 6 and the analyte stage 80 shown in FIG. 8 each include at least one tuning device 16 that includes a piezoelectric material. Other means for tuning a resonant cavity such as, for example, electrostatic forces may be used in analyte stages that embody teachings of the present invention.

Figure 9:
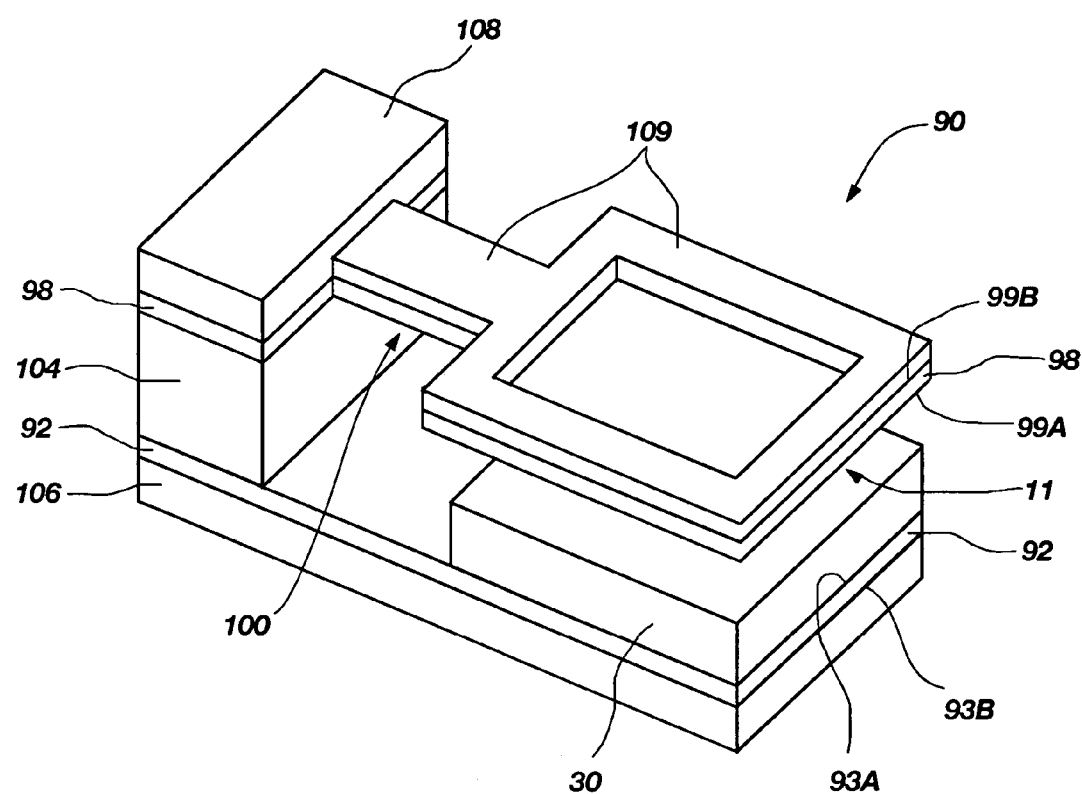
FIG. 9 is a perspective view of another embodiment of an analyte stage of the present invention.

Yet another embodiment of an analyte stage 90 of the present invention is shown in FIG. 9. The analyte stage 90 includes a tunable resonant cavity 11 that includes a first mirror 92 and a second mirror 98. The first mirror 92 and the second mirror 98 each may be substantially planar, and the second mirror 98 may be oriented substantially parallel relative to the first mirror 92. The first mirror 92 may include a first major surface 93A and a second major surface 93B. Similarly, the second mirror 98 may include a first major surface 99A and a second major surface 99B. The first mirror 92 and the second mirror 98 each may include a material that is substantially transparent to wavelengths of electromagnetic radiation that are within an operating range of wavelengths of the tunable resonant cavity 11. For example, the first mirror 92 and the second mirror 98 each may include silica, diamond or a transparent polymer material. A thin layer of reflective material may be provided on at least a portion of a surface of each of the first mirror 92 and the second mirror 98. For example, a thin layer of platinum or silver may be applied to each of the first major surface 93A of the first mirror 92 and the first major surface 99A of the second mirror 98. Furthermore, the reflectivity of the second mirror 98 may be less than one-hundred percent.

An electrically insulating support member 104 may be disposed between at least a portion of the first mirror 92 and at least a portion of the second mirror 98. The electrically insulating support member 104 may be formed from any nonconductive material including, but not limited to, silica or epoxy. The second mirror 98 may be cantilevered relative to the electrically insulating support member 104 to suspend at least a portion of the second mirror 98 above or relative to at least a portion of the first mirror 92. The second mirror 98 may include a thin, narrow region 100 to facilitate deflection of the portion of the second mirror 98 that is suspended above the first mirror 92 relative to the first mirror 92.

At least a portion of a transparent substrate 30 may be provided within the tunable resonant cavity 11 between the first mirror 92 and the portion of the second mirror 98 that is suspended above the first mirror 92. As previously discussed, the transparent substrate 30 may include a material that is substantially transparent to wavelengths of electromagnetic radiation that are within an operating range of wavelengths of the tunable resonant cavity 11.

The analyte stage 90 also may include an electrical contact 108 that is electrically continuous with an electrically conductive structure 109 that extends at least partially over the portion of the second mirror 98 that is suspended above the first mirror 92. By way of example and not limitation, the electrically conductive structure 109 may include a substantially frame-shaped structure disposed on the portion of the second mirror 98 that is suspended above the first mirror 92. The electrically conductive structure 109 may also include a section extending along the thin, narrow region 100 of the second mirror 98 between the electrical contact 108 and the frame-shaped structure. Furthermore, at least a portion of the first mirror 92 may be disposed on a layer of electrically conductive material 106. The electrical contact 108, the electrically conductive structure 109, and the layer of electrically conductive material 106 each may include any electrically conductive material including, but not limited to, gold, copper, platinum, silver, and other metals and alloys.

Figure 10:
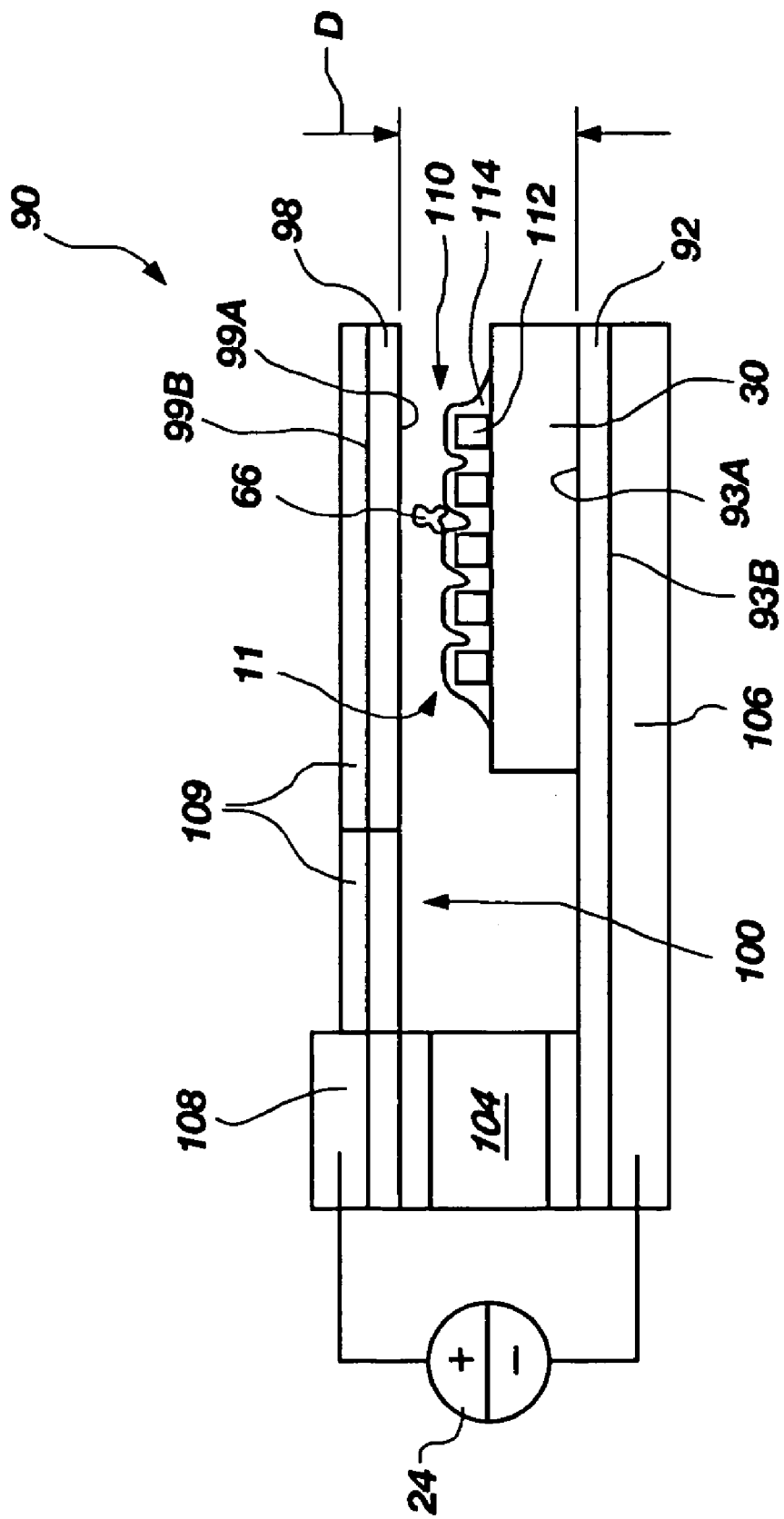
FIG. 10 is a side view of the analyte stage shown in FIG. 9.

As seen in FIG. 10, a Raman signal-enhancing structure 110 may be at least partially disposed within the tunable resonant cavity 11. The Raman signal-enhancing structure 110 may include a plurality of nanoparticles 112 that have been at least partially coated with a Raman signal-enhancing material 114. For example, the nanoparticles 112 may include silica, and the Raman signal-enhancing material 114 may include gold, silver, or platinum. The Raman signal-enhancing structure 110 may be located at any position within the tunable resonant cavity 11. To position the Raman signal-enhancing structure 110 within the tunable resonant cavity 11, the Raman signal-enhancing structure 110 may be provided on a transparent substrate 30 having a predetermined thickness, as previously described in relation to the analyte stage 10 shown in FIG. 2.

The analyte stage 90 may be formed using known techniques for microdevice and nanodevice fabrication on a support substrate, such as, for example, a silicon wafer, partial wafer, or a glass substrate. Examples of techniques for depositing material layers include, but are not limited to, molecular beam epitaxy (MBE), atomic layer deposition (ALD), chemical vapor deposition (CVD), physical vapor deposition (PVD), sputter deposition and other known layer deposition techniques. Photolithography may be used, for example, to pattern features in layers of the device as they are being formed. Examples of techniques that can be used for selectively removing portions of the layers include, but are not limited to, wet etching, dry etching, plasma etching, ion beam etching, electron beam etching, and other known etching techniques. These techniques are known in the art.

The second mirror 98 may be separated from the first mirror 92 by a distance D. The distance D may be varied by providing a power source 24 and applying electrical charge to the first mirror 92 by way of the layer of electrically conductive material 106, and applying electrical charge to the second mirror 98 using the electrical contact 108 and the electrically conductive structure 109. Electrical charge may accumulate within or on a surface of the first mirror 92, and opposite electrical charge may accumulate within or on a surface of the second mirror 98. When the electrical charge on the first mirror 92 is opposite the electrical charge on the second mirror 98, an attractive electrostatic force may be applied to or between the first mirror 92 and the second mirror 98, thereby causing at least a portion of the second mirror 98 to deflect towards the first mirror 92 and the distance D separating that portion of the second mirror 98 from the first mirror 92 to decrease. Similarly, when the electrical charge on the first mirror 92 is the same as the electrical charge on the second mirror 98, a repulsive electrostatic force may be applied to or between the first mirror 92 and the second mirror 98, thereby causing at least a portion of the second mirror 98 to deflect away from the first mirror 92 and the distance D separating that portion of second mirror 98 from the first mirror 92 to increase. In this manner, electrostatic forces may be used as a means for tuning the tunable resonant cavity 11.

Raman spectroscopy may be performed on an analyte 66 the analyte stage 90 in substantially the same manner previously described in relation to the analyte stage 10 shown in FIG. 6. In particular, an analyte 66 may be provided within the tunable resonant cavity 11 proximate the Raman signal-enhancing structure 110, as shown in FIG. 10. The analyte 66 may be irradiated with incident electromagnetic radiation provided by an electromagnetic radiation source. The incident electromagnetic radiation may impinge directly on the analyte 66 without first passing through the first mirror 92 or the second mirror 98. A lateral side of the transparent substrate 30 may be irradiated with incident electromagnetic radiation. The incident electromagnetic radiation may propagate through the transparent substrate 30, and may experience total internal reflection within the substrate 30. Evanescent fields at the surface of the substrate 30 generated by the incident electromagnetic radiation excite the analyte 66.

Raman scattered radiation may be scattered by the analyte 66 within the tunable resonant cavity 11. The tunable resonant cavity 11 may behave as a Fabry-Perot resonator. Raman scattered radiation that is scattered by the analyte in directions substantially perpendicular to the first mirror 92 and the second mirror 98 may reflect back and forth between the first mirror 92 and the second mirror 98. If the distance D separating the second mirror 98 from the first mirror 92 is not equal to an integer multiple of one-half of the wavelength of the Raman scattered radiation, the rays of Raman scattered radiation reflecting back and forth may interfere destructively. If, however, the distance D separating the second mirror 98 from the first mirror 92 is equal to an integer multiple of one-half of the wavelength of the Raman scattered radiation 58, the rays of Raman scattered radiation reflecting back and forth may interfere constructively, thereby increasing the intensity or power of the Raman scattered radiation within the tunable resonant cavity 11. As the reflectivity of the second mirror 98 is less than one-hundred percent, some of the resonating Raman scattered radiation may pass through the second mirror and may be detected.

While the analyte 66 is being irradiated with incident electromagnetic radiation or evanescent electromagnetic radiation, the distance D separating the second mirror 98 from the first mirror 92 may be selectively varied by selectively controlling the quantity and polarity of the charge applied to the first mirror 92 and the second mirror 98 using the power source 24 until the tunable resonant cavity 11 is tuned to resonate the various wavelengths of Raman scattered radiation that are scattered by the analyte 66. For example, the distance D may be may be selectively continuously varied between the maximum distance D defining the upper limit of operation of the tunable resonant cavity 11 and the minimum distance D defining the lower limit of operation of the tunable resonant cavity 11. The Raman scattered radiation may be continuously detected while selectively continuously varying the distance D. In this manner, a unique Raman spectral graph of the analyte 66 may be obtained and used to identify or characterize the analyte 66.

Chemical species or receptors that bind or interact both with a Raman signal-enhancing structure and an analyte may be provided and used with analyte stages and systems that embody teachings of the present invention to promote adherence of the analyte to the analyte stage proximate the Raman signal-enhancing structure.

In addition to Raman spectroscopy systems, analyte stages that embody teachings of the present invention may be used in other types of spectroscopy systems in which electromagnetic radiation emitted by an analyte is to be detected and used to provide information about the analyte. In such other spectroscopy systems, analyte stages that embody teachings of the present invention may be used to resonate the electromagnetic radiation emitted by the analyte in a tunable resonant cavity, thereby enhancing the intensity of the electromagnetic radiation to be detected.

The structures, systems, and methods described herein may be used to enhance the intensity of the Raman signal provided by an analyte, thereby improving the sensitivity of Raman spectroscopy systems relative to currently available Raman spectroscopy systems. Furthermore, the structures, systems, and methods described herein may be used to eliminate the need for a wavelength dispersion grating in Raman spectroscopy systems, thereby decreasing the overall size of Raman spectroscopy systems relative to currently available Raman spectroscopy systems.

The structures, systems, and methods described herein may be used to detect hyper Raman scattered radiation in addition to $1^{st}$ order Raman scattered radiation.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. An analyte stage for use in a spectroscopy system, the analyte stage comprising:
    a resonant cavity, the resonant cavity being capable of resonating electromagnetic radiation having a wavelength less than about 10,000 nanometers;
    a substrate at least partially disposed within the resonant cavity, at least a portion of the substrate disposed within the resonant cavity comprising a base material selectively doped with a dopant that will inelastically scatter electromagnetic radiation at a known wavelength between 100 nanometers and about 10,000 nanometers, the dopant dispersed within the base material; and
    a Raman signal-enhancing structure at least partially disposed within the resonant cavity.

2. The analyte stage of claim 1, wherein the tunable resonant cavity comprises:
a first mirror;
a second mirror, the second mirror being separated from the first mirror by a distance, the second mirror having a reflectivity of less than one-hundred percent; and
a device configured to selectively vary the distance separating the second mirror from the first mirror between a first distance and a second distance.

3. The analyte stage of claim 2, wherein the device configured to selectively vary the distance separating the second mirror from the first mirror comprises a piezoelectric material.

4. The analyte stage of claim 2, wherein the substrate comprises a substantially planar layer of material disposed between the first mirror and the second mirror.

5. The analyte stage of claim 2, wherein the first mirror and the second mirror are substantially planar, the second mirror being oriented substantially parallel to the first mirror.

6. The analyte stage of claim 2, wherein the device configured to selectively vary the distance separating the second mirror from the first mirror comprises means for applying a static electrical force to at least one of the first mirror and the second mirror.

7. The analyte stage of claim 6, wherein the means for applying a static electrical force comprise:
a first electrically conductive structure attached to the first mirror;
a second electrically conductive structure attached to the second mirror; and
an electrical power source electrically coupled to the first electrically conductive structure and the second electrically conductive structure.

8. The analyte stage of claim 1, wherein the dopant comprises $C_{60}$.

9. The analyte stage of claim 1, wherein the Raman signal-enhancing structure comprises a plurality of nanowires or a plurality of nanospheres.

10. A system for performing spectroscopy on an analyte, the system comprising:
an analyte stage comprising:
a resonant cavity, the resonant cavity being capable of resonating electromagnetic radiation having a wavelength less than 10,000 nanometers;
a substrate at least partially disposed within the resonant cavity, at least a portion of the substrate disposed within the resonant cavity being transparent to electromagnetic radiation having wavelengths between 100 nanometers and 10,000 nanometers, the at least a portion of the substrate disposed within the resonant cavity comprising a base material selectively doped with at least one dopant that will inelastically scatter electromagnetic radiation at a known wavelength between 100 nanometers and 10,000 nanometers, the dopant dispersed within the base material; and
a Raman signal-enhancing structure at least partially disposed within the resonant cavity;
a source oriented to emit incident radiation toward the analyte stage; and
a detector configured to detect Raman scattered radiation that is scattered by an analyte.

11. The system of claim 10, wherein the resonant cavity of the analyte stage comprises a tunable resonant cavity, the tunable resonant cavity comprising:
a first mirror;
a second mirror, the second mirror being separated from the first mirror by a distance, the second mirror having a reflectivity of less than one-hundred percent; and
a device configured to selectively vary the distance separating the second mirror from the first mirror between a first distance and a second distance.

12. The system of claim 11, wherein the source is configured to irradiate an analyte positioned between the first mirror and the second mirror with the incident radiation, the incident radiation impinging on the analyte without first passing through the first mirror or the second mirror.

13. The system of claim 11, wherein the substrate is configured to transmit incident radiation between the source and the resonant cavity.

14. The system of claim 11, wherein the first mirror and the second mirror are substantially planar, the second mirror being oriented substantially parallel to the first mirror.

15. The system of claim 10, wherein the Raman signal-enhancing structure comprises a non-enhanced Raman spectroscopy active structure.

16. A method of performing Raman spectroscopy on an analyte, the method comprising:
providing an analyte stage comprising:
providing a resonant cavity, the resonant cavity being capable of resonating electromagnetic radiation having a wavelength less than 10,000 nanometers;
providing a Raman signal-enhancing structure at least partially within the resonant cavity;
and providing a substrate at least partially disposed within the resonant cavity, at least a portion of the substrate disposed within the resonant cavity comprising a base material selectively doped with a dopant that will inelastically scatter electromagnetic radiation at a known wavelength between 100 nanometers and 10,000 nanometers;
providing an analyte within the resonant cavity proximate the Raman signal-enhancing structure;
irradiating the analyte with incident electromagnetic radiation;
detecting Raman scattered radiation that is scattered by the analyte;
detecting Raman scattered radiation that is scattered by the dopant at a known wavelength between 100 nanometers and 10,000 nanometers; and
calibrating at least one component of a Raman spectroscopy system used to perform the Raman spectroscopy on the analyte using the Raman scattered radiation that is scattered by the dopant at the known wavelength.

17. The method of claim 16, wherein providing a resonant cavity comprises:
providing a first mirror;
providing a second mirror, the second mirror having a reflectivity of less than one-hundred percent; and
positioning the second mirror proximate the first mirror, the second mirror being separated from the first mirror by a distance.

18. The method of claim 16, wherein detecting Raman scattered radiation that is scattered by the dopant comprises detecting Raman scattered radiation that is scattered by at least one molecule.

19. The method of claim 18, further comprising selectively varying a resonant that is scattered by at least one molecule.

20. The method of claim 19, wherein irradiating the analyte with electromagnetic radiation comprises:
irradiating a surface of the substrate with the electromagnetic radiation, the electromagnetic radiation impinging directly on the surface of the substrate without first passing through the first mirror or the second mirror;
transmitting the electromagnetic radiation through the at least a portion of the substrate disposed within the resonant cavity; and
subjecting the analyte to evanescent electromagnetic radiation at a surface of the substrate, the evanescent electromagnetic radiation originating from the electromagnetic radiation being transmitted through the at least a portion of the substrate disposed within the resonant cavity.

21. The method of claim 16, wherein providing a Raman signal-enhancing structure at least partially within the resonant cavity comprises providing a nano-enhanced Raman spectroscopy active structure within the resonant cavity.

* * * * *

UNITED STATES PATENT AND TRADEMARK OFFICE
CERTIFICATE OF CORRECTION

PATENT NO. : 7,511,808 B2  
APPLICATION NO. : 11/414077  
DATED : March 31, 2009  
INVENTOR(S) : William M. Tong et al.

Page 1 of 1

It is certified that error appears in the above-identified patent and that said Letters Patent is hereby corrected as shown below:

In column 16, line 58, in Claim 1, after "than" delete "about".

In column 16, line 64, in Claim 1, after "and" delete "about".

In column 17, line 1, in Claim 2, after "wherein the" delete "tunable".

In column 18, line 20, in Claim 15, delete "non-enhanced" and insert -- nano-enhanced --, therefor.

In column 18, line 63, in Claim 19, delete "that is scattered by at least one molecule." and insert -- wavelength of the resonant cavity. --, therefor.

Signed and Sealed this

Sixth Day of October, 2009

David J. Kappos  
*Director of the United States Patent and Trademark Office*